(12) United States Patent
Biedermann et al.

(10) Patent No.: US 11,751,918 B2
(45) Date of Patent: Sep. 12, 2023

(54) COUPLING DEVICE FOR USE WITH A BONE ANCHORING ELEMENT AND BONE ANCHORING DEVICE WITH SUCH A COUPLING DEVICE

(71) Applicant: BIEDERMANN TECHNOLOGIES GMBH & CO. KG, Donaueschingen (DE)

(72) Inventors: Lutz Biedermann, VS-Villingen (DE); Berthold Dannecker, St. Georgen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 17/195,120

(22) Filed: Mar. 8, 2021

(65) Prior Publication Data
US 2021/0282819 A1    Sep. 16, 2021

Related U.S. Application Data

(60) Provisional application No. 62/988,540, filed on Mar. 12, 2020.

(30) Foreign Application Priority Data

Mar. 12, 2020 (EP) .................................... 20162697

(51) Int. Cl.
*A61B 17/70*    (2006.01)
*A61B 17/56*    (2006.01)

(52) U.S. Cl.
CPC ...... *A61B 17/7038* (2013.01); *A61B 17/7032* (2013.01); *A61B 17/7037* (2013.01); *A61B 2017/564* (2013.01)

(58) Field of Classification Search
CPC ............ A61B 17/7038; A61B 17/7032; A61B 17/7035; A61B 17/7037
See application file for complete search history.

(56) References Cited

U.S. PATENT DOCUMENTS 5,429,639 A    7/1995  Judet
5,584,834 A   12/1996  Errico
(Continued)

FOREIGN PATENT DOCUMENTS

DE    102017124734 A1 *  4/2019  ......... A61B 17/7041
EP    2 022 423 A1        2/2009
(Continued)

OTHER PUBLICATIONS

Extended European Search Report for European Application No. 12178289.0, European Search Report dated Nov. 20, 2012 dated Dec. 6, 2012 (7 pgs.).
(Continued)

*Primary Examiner* — Lynnsy M Summitt
(74) *Attorney, Agent, or Firm* — Lewis Roca Rothgerber Christie LLP

(57) ABSTRACT

A coupling device for use with a bone anchoring element includes a receiving part having first and second ends, a longitudinal axis, and a coaxial passage, and a pressure member having a first portion and an expandable portion connected axially to the first portion forming a seat for the head. The pressure member is movable to a position where the receiving part acts on the expandable portion to clamp the head in the seat. The seat can be asymmetric relative to the longitudinal axis while a central axis of the first portion is coaxial with the longitudinal axis, such that the seat facilitates pivoting of the bone anchoring element in a first (Continued)

US 11,751,918 B2

Page 2 direction to a first maximum angle and in an opposite direction to a second maximum angle smaller than the first maximum angle.

25 Claims, 10 Drawing Sheets

(56) References Cited

U.S. PATENT DOCUMENTS

| | | | | |
|---|---|---|---|---|
| 5,672,176 | A * | 9/1997 | Biedermann | A61B 17/7032 606/65 |
| 5,797,911 | A | 8/1998 | Sherman | |
| 5,879,350 | A * | 3/1999 | Sherman | A61B 17/7037 606/270 |
| 5,882,350 | A * | 3/1999 | Ralph | A61B 17/7037 606/278 |
| 5,964,760 | A * | 10/1999 | Richelsoph | A61B 17/7037 606/278 |
| 6,063,090 | A * | 5/2000 | Schlapfer | A61B 17/7037 606/270 |
| 6,074,391 | A * | 6/2000 | Metz-Stavenhagen | A61B 17/7032 606/278 |
| 6,280,442 | B1 | 8/2001 | Barker | |
| 6,736,820 | B2 | 5/2004 | Biedermann | |
| 6,974,460 | B2 | 12/2005 | Carbone | |
| 7,081,116 | B1 | 7/2006 | Carly | |
| 7,678,137 | B2 * | 3/2010 | Butler | A61B 17/7034 606/246 |
| 7,766,944 | B2 * | 8/2010 | Metz-Stavenhagen | A61B 17/7037 606/266 |
| 7,789,900 | B2 * | 9/2010 | Levy | A61B 17/7037 606/300 |
| 8,002,806 | B2 * | 8/2011 | Justis | A61B 17/7038 606/264 |
| 8,016,862 | B2 * | 9/2011 | Felix | A61B 17/7032 606/270 |
| 8,021,397 | B2 * | 9/2011 | Farris | A61B 17/7041 606/269 |
| 8,100,946 | B2 * | 1/2012 | Strausbaugh | A61B 17/7038 606/266 |
| 8,192,470 | B2 * | 6/2012 | Biedermann | A61B 17/7034 606/265 |
| 8,197,517 | B1 * | 6/2012 | Lab | A61B 17/864 606/268 |
| 8,361,129 | B2 * | 1/2013 | Chao | A61B 17/7037 606/305 |
| 8,382,805 | B2 * | 2/2013 | Wang | A61B 17/7037 606/267 |
| 8,444,681 | B2 * | 5/2013 | Jackson | A61B 17/7037 606/300 |
| 8,628,558 | B2 * | 1/2014 | Harvey | A61B 17/7037 606/267 |
| 8,636,778 | B2 * | 1/2014 | Gephart | A61B 17/7082 606/279 |
| 8,709,051 | B2 * | 4/2014 | Hammer | A61B 17/7034 606/272 |
| 8,808,330 | B2 * | 8/2014 | Biedermann | A61B 17/7011 606/264 |
| 8,876,874 | B2 * | 11/2014 | Abdou | A61B 17/7038 606/305 |
| 8,951,290 | B2 * | 2/2015 | Hammer | A61B 17/7035 606/267 |
| 8,979,904 | B2 * | 3/2015 | Jackson | A61B 17/8605 606/260 |
| 9,084,634 | B1 * | 7/2015 | Lab | A61B 17/7002 |
| 9,131,971 | B2 * | 9/2015 | Biedermann | A61B 17/7032 |
| 9,277,942 | B2 | 3/2016 | Biedermann et al. | |
| 9,282,998 | B2 * | 3/2016 | Schlaepfer | A61B 17/7032 |
| 9,320,546 | B2 * | 4/2016 | Keyer | A61B 17/7037 |
| 9,339,304 | B2 * | 5/2016 | Biedermann | A61B 17/7037 |
| 9,439,680 | B2 * | 9/2016 | Biedermann | A61B 17/7032 |
| 9,445,847 | B2 * | 9/2016 | Biedermann | A61B 17/86 |
| 9,452,006 | B2 * | 9/2016 | Biedermann | A61B 17/7038 |
| 9,480,517 | B2 * | 11/2016 | Jackson | A61B 17/7005 |
| 9,486,246 | B2 * | 11/2016 | Biedermann | A61B 17/7037 |
| 9,492,204 | B2 * | 11/2016 | Biedermann | A61B 17/7035 |
| 9,526,531 | B2 * | 12/2016 | Richelsoph | A61B 17/7011 |
| 9,566,092 | B2 * | 2/2017 | Jackson | A61B 17/7037 |
| 9,597,120 | B2 * | 3/2017 | Biedermann | A61B 17/7037 |
| 9,649,134 | B2 * | 5/2017 | Hannen | A61B 17/7032 |
| 9,717,534 | B2 | 8/2017 | Jackson et al. | |
| D799,949 | S | 10/2017 | Stevenson et al. | |
| 9,839,446 | B2 * | 12/2017 | Biedermann | A61B 17/7037 |
| 9,943,338 | B2 * | 4/2018 | Biedermann | A61B 17/7035 |
| 9,993,270 | B2 * | 6/2018 | Butler | A61B 17/7035 |
| 10,058,367 | B2 * | 8/2018 | Biedermann | A61B 17/8605 |
| 10,603,082 | B2 | 3/2020 | Lish | |
| 10,603,083 | B1 * | 3/2020 | Gladieux | A61B 17/7002 |
| 10,918,418 | B2 * | 2/2021 | Murabayashi | A61B 17/7032 |
| 10,918,419 | B2 * | 2/2021 | Kishan | A61B 17/7037 |
| 2002/0091386 | A1 | 7/2002 | Martin | |
| 2003/0055426 | A1 | 3/2003 | Carbone | |
| 2003/0187433 | A1 | 10/2003 | Lin | |
| 2004/0102781 | A1 | 5/2004 | Jeon | |
| 2005/0038430 | A1 | 2/2005 | McKinley | |
| 2005/0080415 | A1 * | 4/2005 | Keyer | A61B 17/7038 606/278 |
| 2005/0154391 | A1 * | 7/2005 | Doherty | A61B 17/7037 606/278 |
| 2005/0154393 | A1 | 7/2005 | Doherty et al. | |
| 2005/0187548 | A1 | 8/2005 | Butler et al. | |
| 2005/0277919 | A1 | 12/2005 | Slivka et al. | |
| 2006/0200128 | A1 * | 9/2006 | Mueller | A61B 17/7037 606/308 |
| 2006/0229615 | A1 | 10/2006 | Abdou | |
| 2006/0264933 | A1 | 11/2006 | Baker | |
| 2006/0276789 | A1 | 12/2006 | Jackson | |
| 2006/0293659 | A1 | 12/2006 | Alvarez | |
| 2007/0173819 | A1 * | 7/2007 | Sandlin | A61B 17/7091 606/278 |
| 2007/0191839 | A1 * | 8/2007 | Justis | A61B 17/7037 606/86 A |
| 2007/0265621 | A1 | 11/2007 | Matthis | |
| 2007/0288004 | A1 * | 12/2007 | Alvarez | A61B 17/7041 606/86 A |
| 2008/0161859 | A1 | 7/2008 | Nilsson | |
| 2008/0177322 | A1 | 7/2008 | Davis | |
| 2008/0234823 | A1 | 9/2008 | Landry et al. | |
| 2008/0269742 | A1 * | 10/2008 | Levy | A61B 17/7032 606/60 |
| 2008/0306513 | A1 | 12/2008 | Winslow et al. | |
| 2009/0069852 | A1 * | 3/2009 | Farris | A61B 17/7037 606/301 |
| 2009/0076550 | A1 | 3/2009 | Bernhardt, Jr. et al. | |
| 2009/0088809 | A1 | 4/2009 | Fisher et al. | |
| 2009/0105770 | A1 * | 4/2009 | Berrevoets | A61B 17/7035 606/308 |
| 2010/0036436 | A1 | 2/2010 | Winslow et al. | |
| 2010/0087867 | A1 | 4/2010 | Klein et al. | |
| 2010/0114180 | A1 * | 5/2010 | Rock | A61B 17/7037 606/308 |
| 2010/0152787 | A1 * | 6/2010 | Walsh | A61B 17/7037 606/308 |
| 2010/0168800 | A1 | 7/2010 | Biedermann | |
| 2010/0298891 | A1 | 11/2010 | Jackson | |
| 2011/0040338 | A1 | 2/2011 | Jackson | |
| 2011/0276098 | A1 | 11/2011 | Biedermann et al. | |
| 2012/0095512 | A1 | 4/2012 | Nihalani | |
| 2012/0123477 | A1 | 5/2012 | Landry | |
| 2012/0185003 | A1 | 7/2012 | Biedermann et al. | |
| 2012/0209335 | A1 | 8/2012 | Termyna et al. | |
| 2012/0209336 | A1 * | 8/2012 | Jackson | A61B 17/7082 606/305 |
| 2012/0303063 | A1 | 11/2012 | Cahill | |
| 2013/0197585 | A1 | 8/2013 | Jackson et al. | |
| 2013/0218213 | A1 | 8/2013 | Lemoine | |
| 2014/0031880 | A1 | 1/2014 | Biedermann et al. | |

(56) References Cited

U.S. PATENT DOCUMENTS

| | | |
|---|---|---|
| 2014/0121703 A1* | 5/2014 | Jackson .............. A61B 17/7032 |
| | | 606/246 |
| 2014/0142633 A1 | 5/2014 | Jackson |
| 2015/0272628 A1* | 10/2015 | Kishan ................ A61B 17/7037 |
| | | 606/279 |
| 2019/0183538 A1 | 6/2019 | Lab et al. |
| 2019/0274734 A1 | 9/2019 | Jackson et al. |
| 2020/0069341 A1 | 3/2020 | Abbasi |
| 2020/0367944 A1* | 11/2020 | Loftis ................. A61B 17/7041 |
| 2021/0106362 A1* | 4/2021 | Jackson .............. A61B 17/7005 |

FOREIGN PATENT DOCUMENTS

| | | |
|---|---|---|
| EP | 2 201 903 A1 | 6/2010 |
| EP | 2 570 090 A1 | 3/2013 |
| EP | 2 586 392 A1 | 5/2013 |
| JP | 2010-533556 A | 10/2010 |
| WO | WO 2009/012247 A1 | 1/2009 |
| WO | WO 2012/048004 A2 | 4/2012 |
| WO | WO 2012/162550 A1 | 11/2012 |

OTHER PUBLICATIONS

Extended European Search Report for European Application No. 20162697.5, dated Oct. 9, 2020, 10 pages.

* cited by examiner

COUPLING DEVICE FOR USE WITH A BONE ANCHORING ELEMENT AND BONE ANCHORING DEVICE WITH SUCH A COUPLING DEVICE

CROSS-REFERENCE TO RELATED APPLICATION(S)

The present application claims priority to and the benefit of U.S. Provisional Patent Application No. 62/988,540, filed Mar. 12, 2020, the contents of which are hereby incorporated by reference in their entirety, and claims priority from European Patent Application EP 20 162 697.5, filed Mar. 12, 2020, the contents of which are hereby incorporated by reference in their entirety.

BACKGROUND

Field

The application relates to a coupling device for use with a bone anchoring element and to a bone anchoring device including the coupling device and the bone anchoring element. The coupling device permits the bone anchoring element to pivot at a greater angle in one direction compared to another direction. A particular application of such a coupling device and bone anchoring device is in spinal surgery.

Description of Related Art

A bone anchoring device is known from U.S. Pat. No. 6,736,820 B2. The bone screw described therein has a screw member and a receiving part, wherein the receiving part has a first bore with a seat for the head at the bottom of the first bore and a second bore. To allow the screw member to be pivoted to at least one side by an enlarged angle, the edge bounding the free end of the second bore viewed relative to the axis of the first bore is of an asymmetric construction.

Another polyaxial bone anchoring device is known from US 2014/0031880 A1. In one embodiment the polyaxial bone anchoring device includes a receiving part for coupling a rod to a bone anchoring element, with a first passage at the bottom end having a first longitudinal axis and a second passage at the top end having a second longitudinal axis that intersects the first longitudinal axis. In the receiving part, a compression element is arranged which has a seat for the head. The polyaxial bone anchoring device provides for an enlarged pivot angle to one side compared to an opposite side, i.e., the device has a favored angle design.

SUMMARY

It is an object of the invention to provide an alternative or improved coupling device and polyaxial bone anchoring device that has a greater field of application.

The coupling device can be used with a bone anchoring element, wherein the bone anchoring element includes a head and a shank for anchoring in bone. The coupling device includes a receiving part configured to receive the head of the bone anchoring element, where the receiving part has a first end and a second end, and a passage extending from the first end to the second end and defining a longitudinal axis, and a pressure member positionable at least partially in the passage and configured to exert pressure onto the head to clamp the head in the receiving part, wherein the pressure member has a central axis which is coincident with the central axis of the receiving part and further has a seat for the head. The seat is configured to pivotably receive the head of the bone anchoring element and is further configured to permit pivoting of the bone anchoring element in at least one direction at a first maximum angle relative to the longitudinal axis and in an opposite direction to the one direction at a second maximum angle relative to the longitudinal axis, wherein the first maximum angle is greater than the second maximum angle, and wherein the second maximum angle is limited by an abutment provided by the pressure member against the bone anchoring element.

A bone anchoring device includes the coupling device and the bone anchoring element, and can be classified as a favored angle type of bone anchoring device. This type may be particularly useful in certain applications, such as in correction techniques carried out on the cervical spine.

The second maximum pivot angle is preferably 0° or about 0° or is limited to a small range of angles between 0° and about 10°, or 0° and about 5° or less, relative to the longitudinal axis of the receiving part. Thus, when the bone anchoring element is pivoted to the second maximum pivot angle, i.e. when it is at or near a zero angle position, the bone anchoring device functions similar to a monoaxial bone anchoring device in which a shank axis is substantially coaxial with the longitudinal axis of the receiving part. The wall thickness in the region of the abutment is sufficiently high so that higher fixation forces may be applied, compared to a polyaxial bone anchoring device in which the zero angle position is not defined by an abutment.

Since the second maximum pivot angle is defined by an abutment provided at the pressure member, the second maximum angle is basically independent of the shape of the receiving part. Various pressure members can be used in combination with a single type of receiving part to achieve various second maximum angles depending on the specific application.

The bone anchoring device may in some embodiments be a top-loading bone anchoring device, in which the bone anchoring element is inserted into the receiving part from the top end thereof.

BRIEF DESCRIPTION OF THE DRAWINGS

Further features and advantages of the invention will become apparent from the description of embodiments by means of the accompanying drawings. In the drawings.

DETAILED DESCRIPTION

Figure 1:
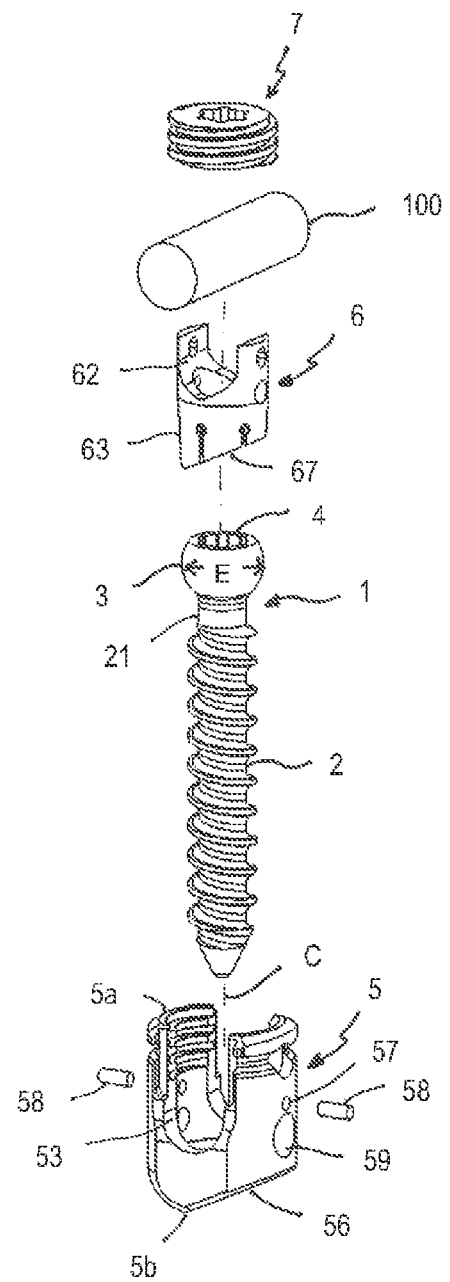
FIG. 1 shows a perspective exploded view of a first embodiment of a bone anchoring device including a coupling device according to a first embodiment.

As shown in FIGS. 1 to 4, a polyaxial bone anchoring device according to a first embodiment includes a bone anchoring element 1 in the form of a bone screw having a shank 2 with a threaded portion and a head 3 with a spherical outer surface portion, more specifically, with a spherical segment-shape. A shank axis S is defined by a longitudinal axis or screw axis of the shank 2. On its free end, the head 3 may have a recess 4 for engagement with a tool. Between the threaded portion of the shank 2 and the head, a thread-free neck portion 21 may be provided. The neck portion 21 may be substantially cylindrical. The bone anchoring device further includes a coupling device for coupling the bone anchoring element 1 to a rod 100. The coupling device includes a receiving part 5 and a pressure member 6 configured to be arranged at least partially in the receiving part 5. The receiving part 5 is configured to receive the rod 100 and to couple the rod 100 to the bone anchoring element 1. The pressure member 6 is configured to accommodate the head 3 of the bone anchoring element 1 and to exert pressure onto the head 3 to clamp and finally lock the head 3 in the receiving part 5. Moreover, a locking element 7 in the form of, for example, an inner screw or set screw which cooperates with the receiving part 5, may be provided for securing and fixing the rod 100 and for locking the head 3 in the receiving part 5.

Referring in greater detail to FIGS. 5 to 8, the receiving part 5 is a substantially cylindrical, preferably monolithic, part and has a first or top end 5a, a second or bottom end 5b and a passage 51 extending from the top end 5a to the bottom end 5b, where it forms an opening 52. The passage 51 defines a central longitudinal axis C. The central longitudinal axis may also define an axis of symmetry for the upper rod receiving portion of the receiving part 5. Several sections of the passage 51 may have different widths and/or shapes, and the passage 51 is not limited to the exact shape shown in the figures. Adjacent to the opening 52, the passage 51 has a slightly tapered section 51a which tapers and narrows, for example, conically towards the bottom end 5b. The tapered section 51a has an axial length or height such that it can receive a portion of the pressure member 6 that includes an accommodation space for an inserted head 3 and exert a compressive force via the pressure member 6 onto the head 3. In the tapered section 51a, an internal thread 510 may be formed to cooperate with a thread on the shank 2. The internal thread can facilitate the insertion of shanks 2 with a larger diameter, which can thereby be screwed through the tapered section 51a. Adjacent to the tapered section 51a, there may be a cylindrical section 51b with a slightly greater width, so that a step 51c is formed between the tapered section 51a and the cylindrical section 51b. The cylindrical section 51b may reach up to the top end 5a. For receiving the rod 100, a substantially U-shaped recess 53 extends from the top end 5a to a distance thereof, preferably to an axial position which still corresponds to the cylindrical section 51b. The substantially U-shaped recess 53 divides the upper portion of the receiving part 5 into two free legs 54 and forms a channel for receiving the rod 100. An internal thread 55 may be provided on the legs 54 that is configured to cooperate with an external thread of the locking member 7.

At the bottom end 5b, the receiving part 5 has an inclined lower surface 56 that may be formed, for example, by cutting away a lower portion of the substantially cylindrical receiving part 5 in an oblique manner in a direction of the top end 5a. The inclined lower surface 56 extends at an angle to the central longitudinal axis C and is preferably oriented towards the middle of one of the legs 54, when viewed in a circumferential direction. As can be best seen in FIGS. 6 and 8, the inclined surface 56 encompasses only a portion of the opening 52, forming an ellipsoidal segment-shaped edge 52b. In the opposite direction of the axially highest position of the inclined surface 56, a circular segment-shaped section of the opening 52 with a circular segment-shaped edge 52a may remain. The inclined surface 56 with the ellipsoidal segment-shaped edge 52b provides an enlarged space for the shank 2 to pivot therein until it abuts against the edge 52b. Thus, the edge 52b is configured to form an abutment for the shank 2 to limit a pivot angle of the bone anchoring element 1, and defines a first maximum pivot angle for the bone anchoring element 1.

The size of the portion of the opening 52 defined by the edge 52a is such that a portion of the pressure member 6 may extend therein to provide a sufficient area for seating the head 3, as explained in greater detail below.

Figure 4:
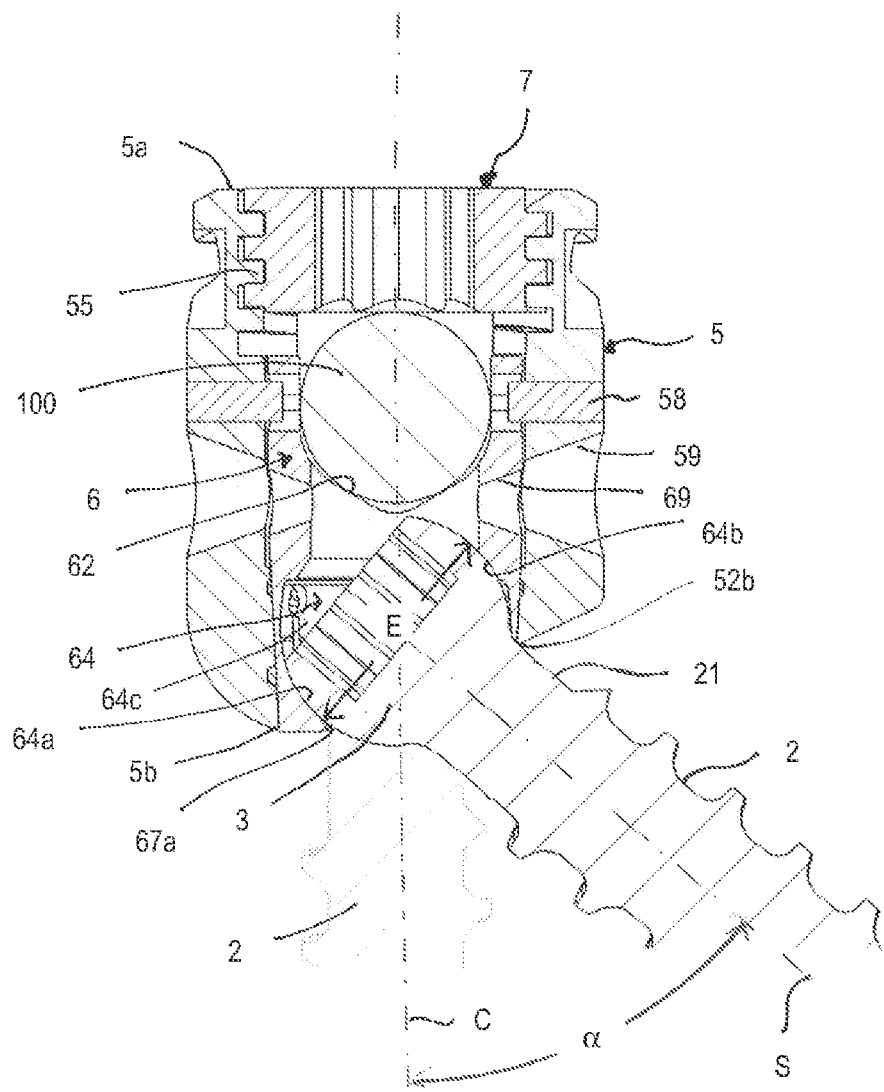
FIG. 4 shows a cross-sectional view of the polyaxial bone anchoring device of FIGS. 1 to 3 in an assembled state, the cross-section taken in a plane including the longitudinal axis of the receiving part and extending through centers of legs of the receiving part.
Figure 5:
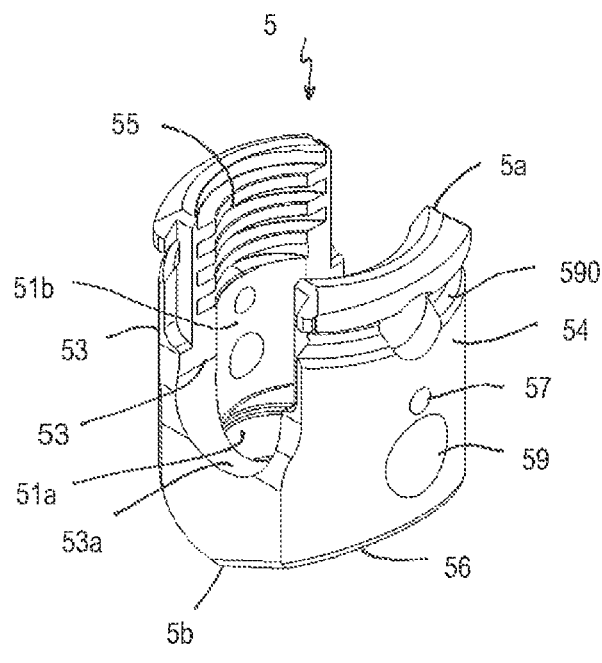
FIG. 5 shows a perspective view from a top of the receiving part of the polyaxial bone anchoring device of FIGS. 1 to 4.
Figure 6:
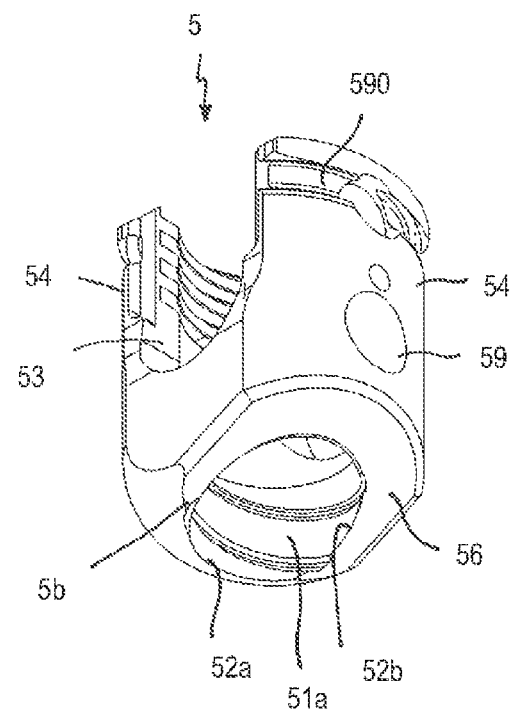
FIG. 6 shows a perspective view of a bottom of the receiving part of FIG. 5.
Figure 7:
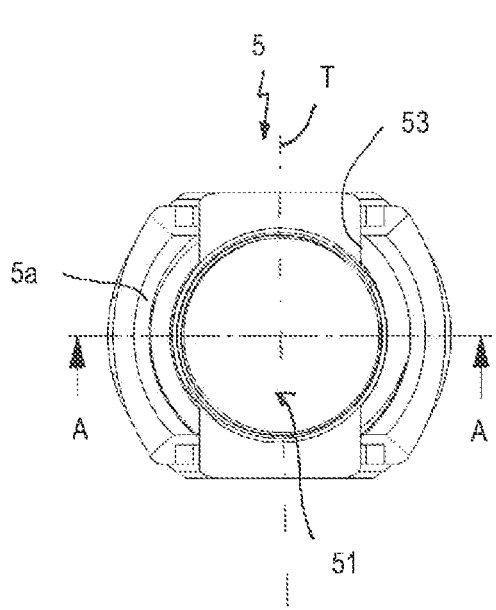
FIG. 7 shows a top view of the receiving part of FIGS. 5 and 6.
Figure 8:
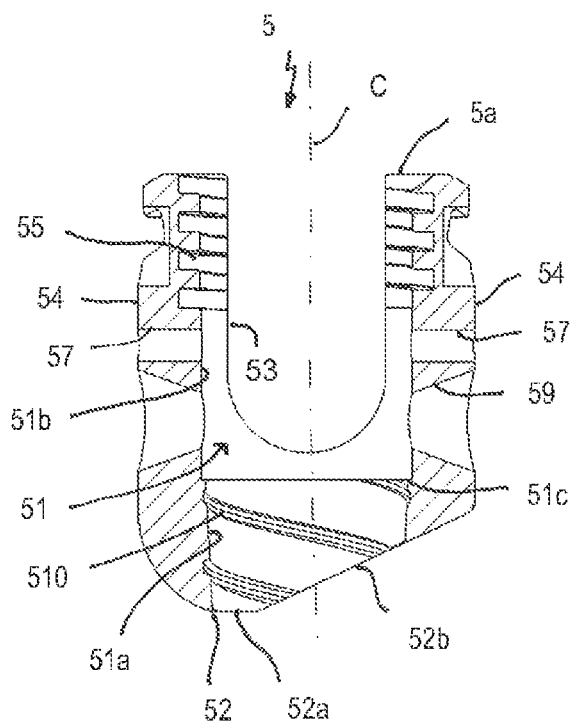
FIG. 8 shows a cross-sectional view of the receiving part of FIGS. 5 to 7, the cross-section taken along line A-A in FIG. 7.
Figure 9:
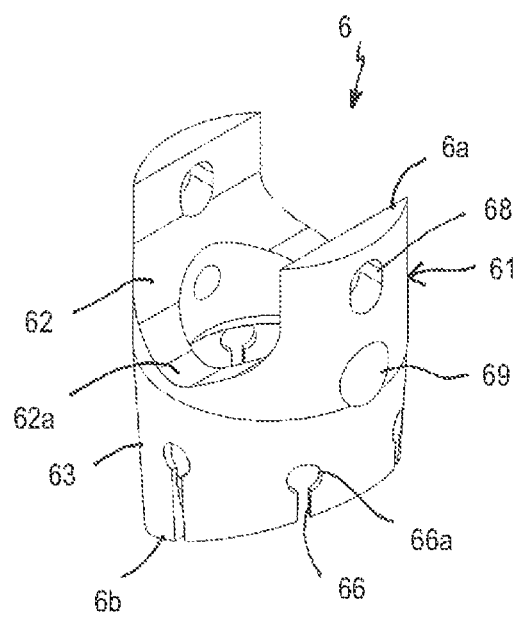
FIG. 9 shows a perspective view from a top of a pressure member of the polyaxial bone anchoring device of FIGS. 1 to 4.
Figure 10:
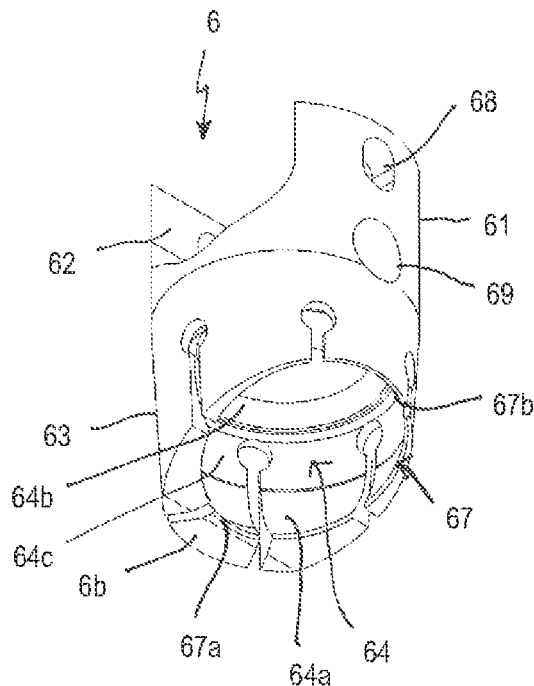
FIG. 10 shows a perspective view from a bottom of the pressure member of FIG. 9.
Figure 11:
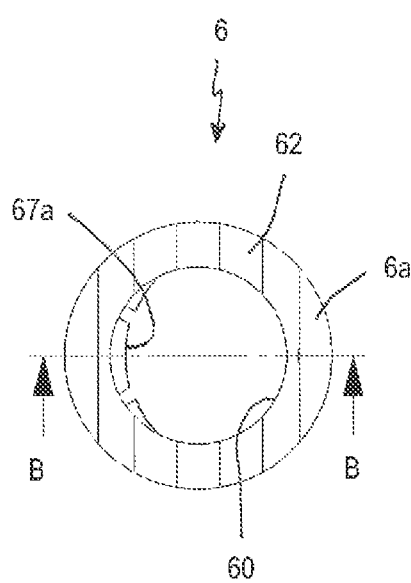
FIG. 11 shows a top view of the pressure member of FIGS. 9 and 10.

At a center of each leg 54, in a circumferential direction and at an axial position above a bottom 53a of the substantially U-shaped recess 53, a pair of through-holes 57 extend through each leg 54. The through-holes 57 are configured to receive pins 58 as shown in FIGS. 1 and 4 for rotationally securing the pressure member 6 in the receiving part 5. Moreover, at the center of each leg 54 and below the through-holes 57, a pair of tool engagement holes 59, preferably conical holes that narrow towards the passage 51, may be formed that allow a tool (not shown) to engage the pressure member 6 to slightly move the pressure member, for example, in a direction towards the top end 5a for unlocking the clamping or locking of the head 3. Finally, optional tool engagement portions 590, such as a circumferential groove and/or central recesses, can be provided at the legs 54 to allow engagement of the receiving part 5 with a tool (not shown).

Referring now in addition to FIGS. 9 to 12, the pressure member 6 will be explained in greater detail. The pressure member 6 of this embodiment may preferably be a monolithic piece. It has a first or top end 6a and an opposite second or bottom end 6b. Adjacent to the top end 6a is an upper portion 61 that may be substantially cylindrical, with an outer diameter which allows it to move in an axial direction in the passage 51 of the receiving part 5. At the top end 6a, a rod-receiving recess 62 is formed that provides a rod support surface. A lower section of the recess 62 may have a substantially V-shaped cross-section with a bottom 62a, where a longitudinal axis of the recess 62 extends substantially perpendicular to a cylinder axis of the pressure member 6. The cylinder axis of the pressure member may substantially coincide with the central longitudinal axis C of the receiving part 5 when the pressure member 6 is in the receiving part 5. A depth of the recess 62 may be smaller than a diameter of the rod 100. Hence, when the rod 100 rests on the support surface, the rod projects over the top end 6a of the pressure member 6 as shown, for example, in FIG. 4. The V-shape of the rod support surface facilitates easier use of rods with different diameters.

A lower portion 63 of the pressure member 6 has a tapered, preferably conical, outer surface which is configured to cooperate with the tapered inner surface of the tapered portion 51a of the passage 51 in the receiving part 5. The tapered outer surface may be continuously joined with the upper cylindrical portion 61. A head receiving recess 64 is formed in the lower portion 63 and extends from the bottom end 6b to a distance from a bottom 62a of the rod receiving recess 62. The head receiving recess 64 has a lower section 64a close to the bottom end 6b that has a substantially hollow spherical shape, with a radius of the sphere matching that of head 3. Furthermore, an uppermost section 64b of the head receiving recess 64 is also hollow spherically-shaped with the same radius as the lower section 64a. By means of this, the lower spherical section 64a and the upper spherical section 64b provide a spherical support for the head 3, and thus form a seat in which the head 3 can pivot. Between these two spherically-shaped sections 64a, 64b, an intermediate widened section 64c may be provided that has a greater inner diameter than the lower end of the upper spherical section 64b. The intermediate widened section 64c may facilitate pivoting of the head 3.

In addition, the lower portion 63 of the pressure member has flexible wall sections 65 that are separated by axial slots 66 open towards the bottom end 6b. To obtain a certain degree of flexibility, the slots 66 may widen towards their closed ends 66a. In the axial direction, the slots 66 may extend preferably up to the transition between the intermediate section 64c and the upper spherical segment-shaped section 64b. The head 3 can be inserted by slightly expanding the flexible wall sections 65. Moreover, the head 3 can be held by friction in the head receiving recess 64 prior to final locking.

The bottom end 6b has an inclined portion, so that an inclined edge 67 encompasses the opening of the head receiving recess 64. The inclined edge 67 may be formed, for example, by cutting away material from the lower portion 63 in an oblique manner. As a result, the inclined edge 67 extends at an angle to the central longitudinal axis C, for example, in the direction of one of the sidewalls of the rod receiving recess 62, and has a substantially ellipsoidal shape. By means of this, the inclined edge 67 provides an enlarged space for the bone anchoring element 1 to pivot to one side, as shown in particular in FIG. 4. A region 67b of the inclined edge which is closest to the top end 6a is, in a mounted configuration of the pressure member 6, substantially aligned with the portion 52b of the opening of the receiving part 5, and allows the shank 2 to pivot to the first maximum pivot angle. The region 67a of the edge 67 opposite to the region 67b defines a second maximum pivot angle to a side opposite to the first maximum pivot angle.

Figure 12:
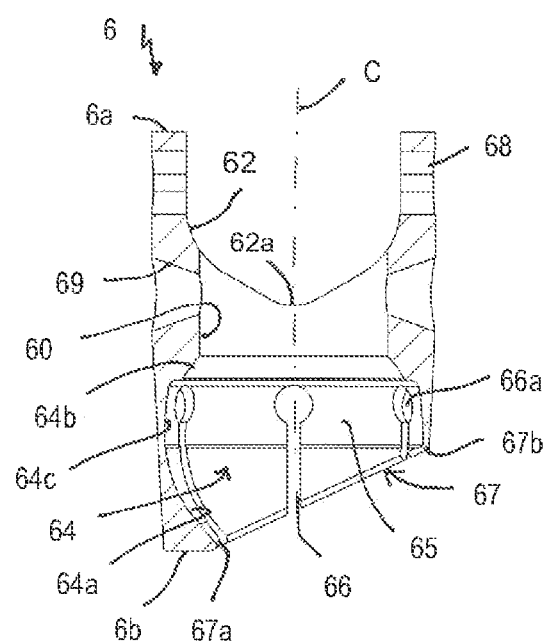
FIG. 12 shows a cross-sectional view of the pressure member of FIGS. 9 to 11, the cross-section taken along line B-B in FIG. 11.
Figure 13:
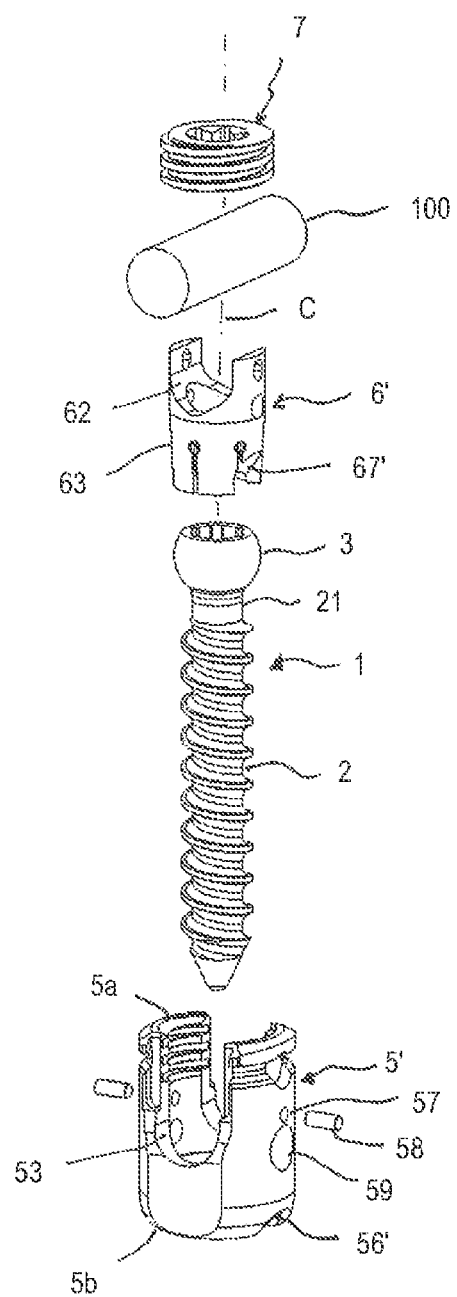
FIG. 13 shows a perspective exploded view of a second embodiment of the polyaxial bone anchoring device, with a second embodiment of the coupling device.

As can be seen in particular in FIGS. 4 and 12, the head receiving recess 64 has a size such that when the head 3 is received in the seat and is in a zero position, i.e., where the shank axis S is substantially coaxial to or otherwise parallel with the central longitudinal axis C, the region 67a of the inclined edge 67 is configured to abut against the shank 2. By means of this, on the one hand a sufficient coverage of the head 3 is provided to form a seat for pivoting. On the other hand, the region 67a of the inclined edge 67 can form an abutment that acts directly on the shank 2, thereby limiting the second pivot angle to 0° or to a small range around 0°. The portion of the lower end 6b around the region 67a has a thickness such that its flexibility is reduced or eliminated. Thereby, the thicker wall produces a sufficient counter-force for high tightening forces when the head is locked in the zero position. It shall be noted that the inclination of the inclined edge 67 may be selected such that there is sufficient hold for the head 3 in the seat, so that the head 3 cannot inadvertently escape from the head receiving recess 64. Preferably, in the zero position, the head 3 is still covered in the head receiving recess 64, such that the edge region 67b opposite to the abutment provided by the edge region 67a is at or below a region of the head 3 including the greatest diameter E of the head.

The pressure member may further include elongate recesses 68 formed in the sidewalls of the rod receiving recess 62. The elongate recesses 68 are oriented with their long side substantially parallel to the central longitudinal axis C. As shown in particular in FIGS. 9 and 12, the elongate recesses 68 extend through the entire sidewall and are configured to receive the pins 58. Thereby, the pressure member 6 can be fixed in its rotational position. Furthermore, an upward and/or downward movement of the pressure member 6 relative to the receiving part is limited by an abutment of the pins 58 against the lower or upper ends of the recesses 68. Finally, a pair of preferably conical recesses 69 are formed in the sidewalls of the rod receiving recess 62 below the elongate recesses 68. The conical recesses 69 narrow towards the rod receiving recess 62, and serve for cooperation with the corresponding recesses 59 at the receiving part and can be engaged by a tool. Lastly, the pressure member 6 has a coaxial bore 60 for allowing access to the head 3, more particularly to the recess 4 of the bone anchoring element 1 with a tool. A cylinder axis of the coaxial bore 60 may define the central longitudinal axis of the pressure member 6, which is configured to be substantially coincident or otherwise parallel with the central longitudinal axis C of the receiving part 5.

The parts and portions of the bone anchoring device may be made of any material, preferably however of titanium or stainless steel, or of any bio-compatible metal or metal alloy or plastic material. For a bio-compatible alloy, a NiTi-alloy, for example Nitinol, may be used. Other materials that can be used are, for example, magnesium or magnesium alloys. Bio-compatible plastic materials that can be used may be, for example, polyether ether ketone (PEEK) or poly-L-lactide acid (PLLA). The various parts can be made of the same or of different materials from one another.

The assembly of the polyaxial bone anchoring device may be such that first, the head 3 is inserted into the head receiving recess 64 of the pressure member 6. Then, the pressure member 6 with bone anchoring element 1 is inserted from the top end 5a into the receiving part 5 in a manner such that the rod receiving recess 62 and the substantially U-shaped recess 53 are aligned. Moreover, the pressure member 6 is orientated in such a manner with respect to the receiving part 5 that the inclined surface 56 of the receiving part and the inclined edge 67 of the pressure member 6 are aligned in the same direction. This rotational position may be secured by the pins 58 extending through the through-holes 57.

Figure 2:
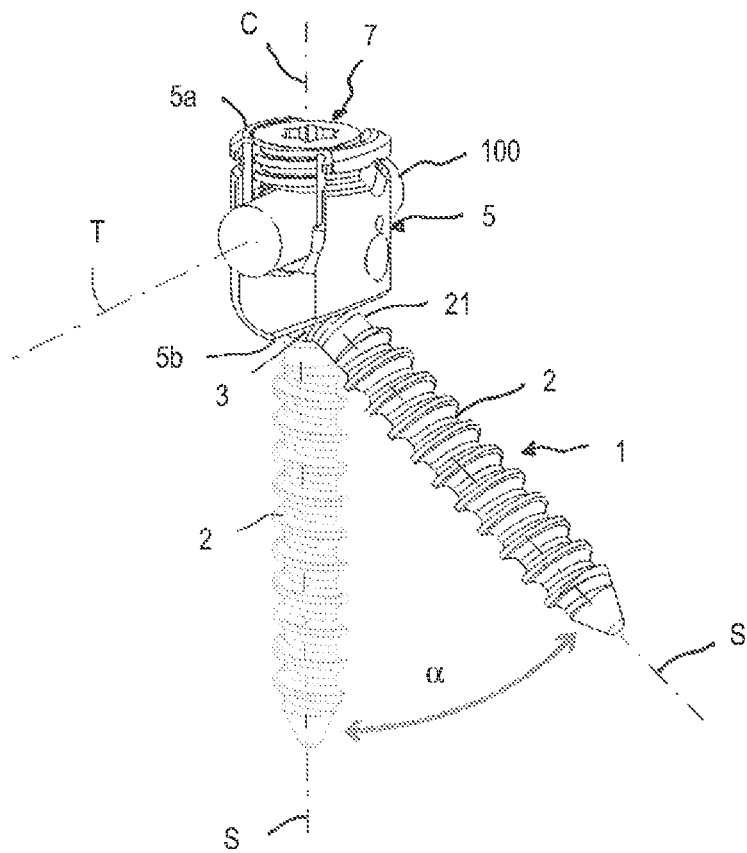
FIG. 2 shows a perspective view from a side of the polyaxial bone anchoring device of FIG. 1 in an assembled state, with a bone anchoring element of the polyaxial bone anchoring device pivoted to a first maximum angle and to a second maximum angle in the opposite direction of the first maximum angle relative to a longitudinal axis of a receiving part of the polyaxial bone anchoring device.
Figure 3:
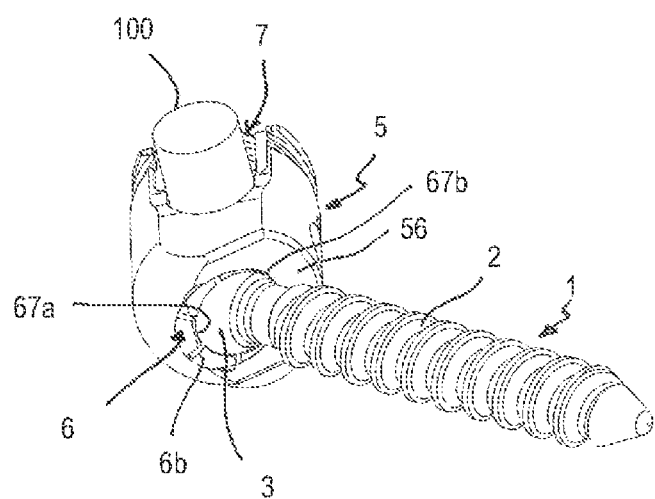
FIG. 3 shows a perspective view from a bottom of the polyaxial bone anchoring device of FIGS. 1 and 2, with the bone anchoring element pivoted to the first maximum pivot angle.

Referring now in greater detail to FIGS. 2 to 4, use of the polyaxial bone anchoring device according to the first embodiment of the invention will be explained. Once the bone anchoring device has been assembled, the bone anchoring element 1 is inserted into bone or a vertebra, for example into the pedicle of a vertebra. Usually, at least two bone anchoring devices are implanted and later connected by the rod 100. As long as the bone anchoring device is not yet finally locked by inserting the rod 100 and fixing it with the locking member 7, the receiving part 5 and the bone anchoring element 1 can be pivoted relative to each other, so that the bone anchoring element 1 can assume various angular positions of the shank axis S with respect to the central longitudinal axis C of the receiving part. In the mounted state, the pressure member 6 can be at a position within the receiving part 5 such that the pressure member is slightly compressed so that the head 3 is held by friction. Depending on the strength of the frictional clamping of the head 3 within the pressure member 6, any pivot position may be maintained provisionally before final locking. In this position, the tool engagement recesses 69 of the pressure member 6 are at a slightly lower axial position than the tool engagement recesses 59 of the receiving part 5.

Pivoting of the coupling device relative to the bone anchoring element will now be described. When the coupling device is pivoted relative to the bone anchoring element 1, more specifically relative to the shank 2, the coupling device can assume a plurality of angular positions relative to the bone anchoring element. By the abutment of the shank 2, in particular the neck portion 21, at the edge portion 52b, a first maximum pivot angle is defined. In FIGS. 2 and 4 the first maximum pivot angle is designated as an angle $\alpha$. The first maximum pivot angle may be up to about 55° relative to the longitudinal axis C, depending on the angle of inclination of the edge portion 52b. When the bone anchoring element pivots in an opposite direction, the shank 2 abuts against the edge region 67a of the pressure member. By this abutment, a second maximum pivot angle is defined in the opposite or counter direction. The second maximum pivot angle is preferably substantially 0°, so that the shank axis S and the central longitudinal axis C are substantially coaxial. In this configuration, the bone anchoring device resembles a monoaxial bone anchoring device. Due to the abutment at the edge region 67a of the pressure member 6, which has a thick stable wall, the bone anchoring device can be tightened with higher tightening forces exerted by the locking member 7.

The highest position of the edge portion 52b is, in this embodiment, at a circumferential position that is 90° from the transverse axis T of the recess 53, or in other words, 90° relative to the rod axis of an inserted rod. It shall be noted that the edge portion 52b of the receiving part and the edge 67 provide an abutment also in cases where the bone anchoring element 1 is pivoted at an angle different from 90° to the transverse axis T or rod axis. Hence, the maximum angle may vary along the edge portion 52b. In addition, the second maximum angle in the opposite direction may be slightly greater than 0°. Therefore, the second maximum angle can be in a range of 0° to a maximum of 10°, preferably a maximum of 5°, or more preferably a maximum of 2° or less, in the opposite direction.

It shall be noted, that the bone anchoring element can also be pivoted to any position between the first maximum angle and the second maximum angle and be fixed there.

After having adjusted the receiving part 5 relative to the bone anchoring element 1, the rod is inserted into the receiving part and the entire bone anchoring device is locked by inserting and tightening the locking member 7. Using an instrument, any provisional clamping or locking can be loosened again. To unlock a provisional or final locking of the head, the instrument can engage the tool engagement recesses 59, 69 of the receiving part 5 and the pressure member 6, and thereby exerts an upwardly directed force onto the pressure member which reduces the pressure onto the head 3.

A second embodiment of the coupling device and the bone anchoring device will be described with reference to FIGS. 13 to 23. The descriptions of parts and portions that are identical or similar to those of the first embodiment will not be repeated. The polyaxial bone anchoring device according to the second embodiment differs from the polyaxial bone anchoring device according to the first embodiment in the shape of the receiving part and of the pressure member.

The receiving part 5' differs from the receiving part 5 in the design of the lower portion that defines the first maximum pivot angle. Referring in greater detail to FIGS. 16 to 19, the receiving part 5' lacks the inclined surface 56 of the first embodiment that is generated by cutting-away a portion of the cylindrical lower end of the receiving part. Instead, the receiving part 5' has a cut-out portion 56'. The cut-out portion 56' is substantially cylinder segment-shaped and has a size such that the neck portion 21 of the shank 2 can extend therein. A central longitudinal axis, more specifically the cylinder axis, of the cut-out portion 56' is inclined relative to the longitudinal axis C, preferably in a manner such that it corresponds substantially to the first maximum pivot angle α. Preferably, the width of the cut-out 56' is such that once the neck portion 21 extends therein, a rotation of the bone anchoring element 1 is hindered. In the embodiment, the orientation of the cut-out portion 56' is in the direction of one of the legs 54, i.e., is arranged at a radial direction that is substantially perpendicular to the transverse axis T or to the rod axis. The cut-out portion 56' may have a bevel 56a' at an outer side thereof. With the cut-out portion 56', the edge of the opening 52 can be divided into a circular segment-shaped portion 52a' that extends around the central longitudinal axis C except in the place of the cut-out portion 56', and the inclined edge 52b' of the cut-out portion that serves as an abutment for the bone anchoring element 1.

By means of this, an enlarged first maximum pivot angle α to one side is defined. Due to the particular orientation of the cut-out portion 56' shown in the embodiment, the first maximum pivot angle is arranged at a radial direction that is 90° with respect to the transverse axis T or rod axis.

Figure 14:
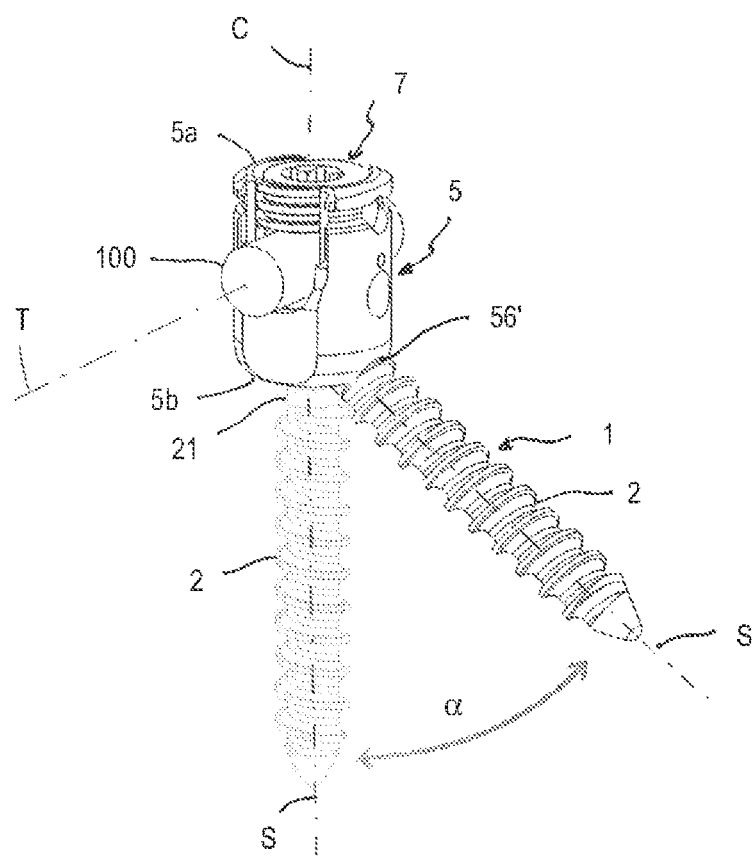
FIG. 14 shows a perspective view from a side of the polyaxial bone anchoring device of FIG. 13 in an assembled state, with a bone anchoring element of the polyaxial bone anchoring device assuming a first maximum angle and a second maximum angle in the opposite direction of the first maximum angle relative to a longitudinal axis of a receiving part of the polyaxial bone anchoring device.
Figure 15:
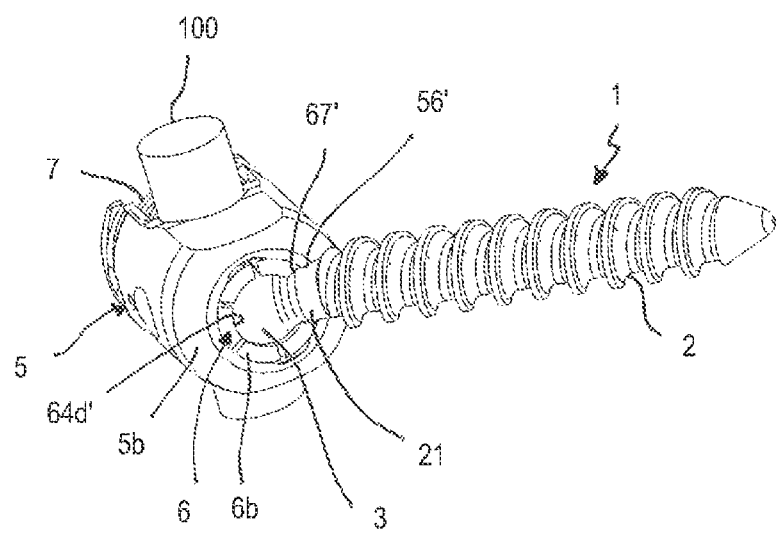
FIG. 15 shows a perspective view from a bottom of the polyaxial bone anchoring device of FIGS. 13 and 14, with the bone anchoring element assuming the first maximum angle relative to the receiving part.
Figure 16:
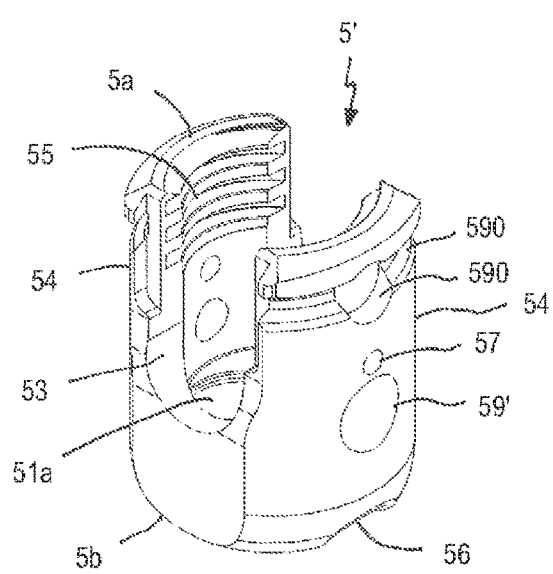
FIG. 16 shows a perspective view from a top of the receiving part of the coupling device of FIGS. 13 to 15.
Figure 17:
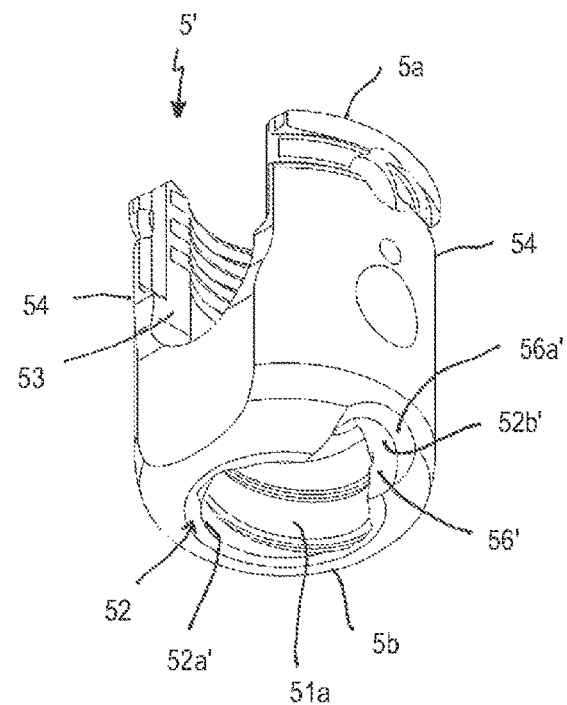
FIG. 17 shows a perspective view from a bottom of the receiving part of FIG. 16.
Figure 18:
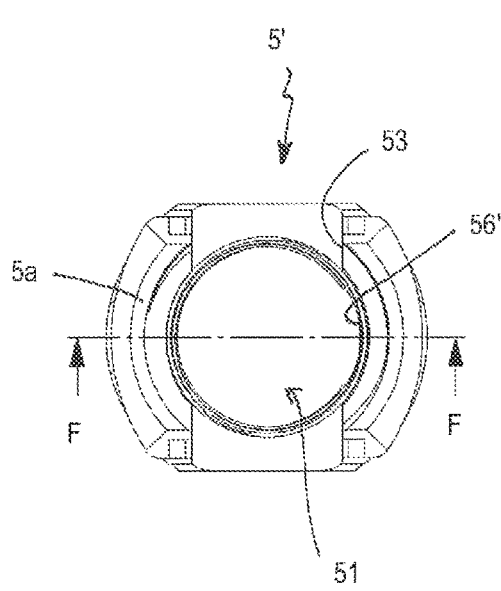
FIG. 18 shows a top view of the receiving part of FIGS. 16 and 17.
Figure 19:
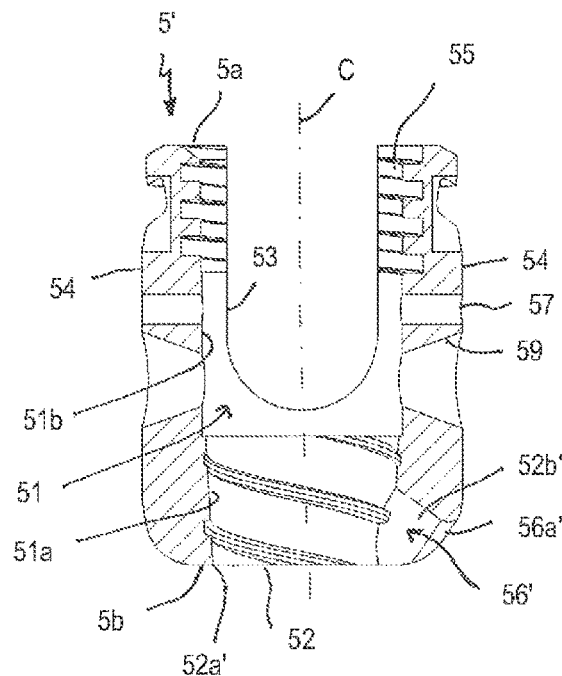
FIG. 19 shows a cross-sectional view of the receiving part of FIGS. 16 to 18, the cross-section taken along line F-F in FIG. 18.
Figure 20:
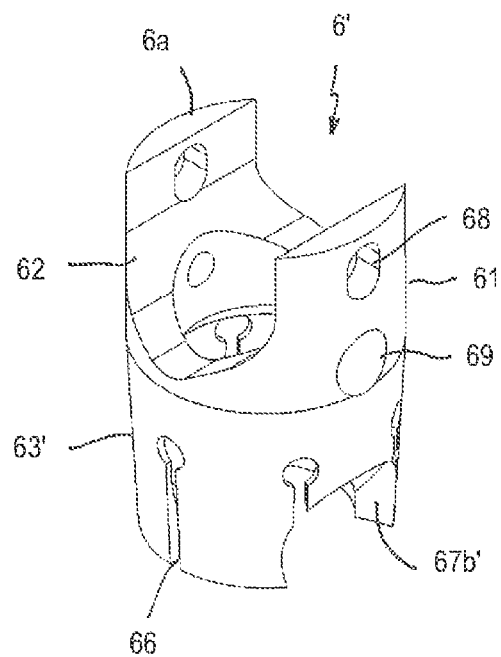
FIG. 20 shows a perspective view from a top of a pressure member of the coupling device of FIGS. 13 to 15.
Figure 21:
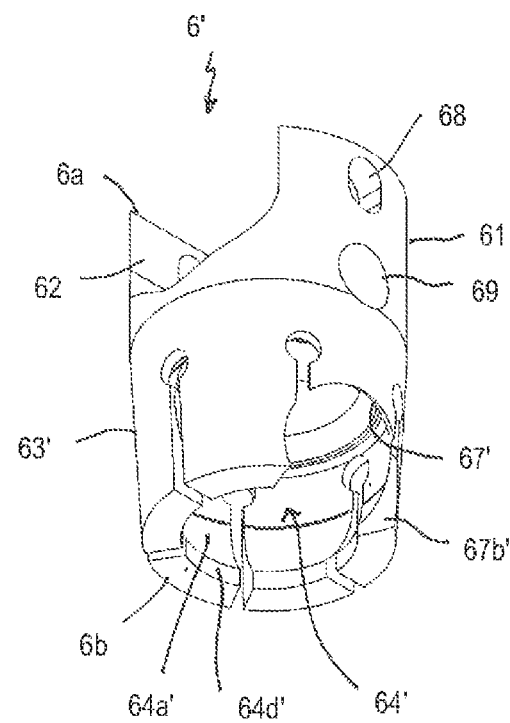
FIG. 21 shows a perspective view from a bottom of the pressure member of FIG. 20.
Figure 22:
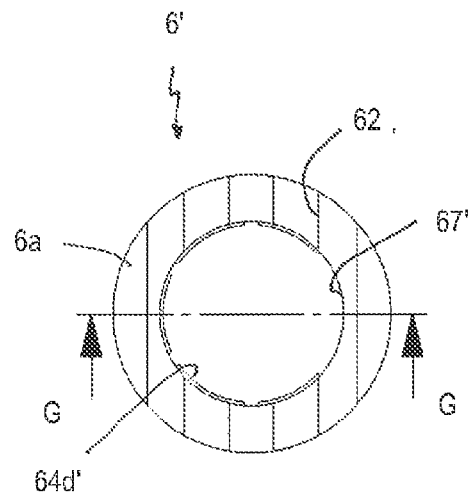
FIG. 22 shows a top view of the pressure member of FIGS. 20 and 21.
Figure 23:
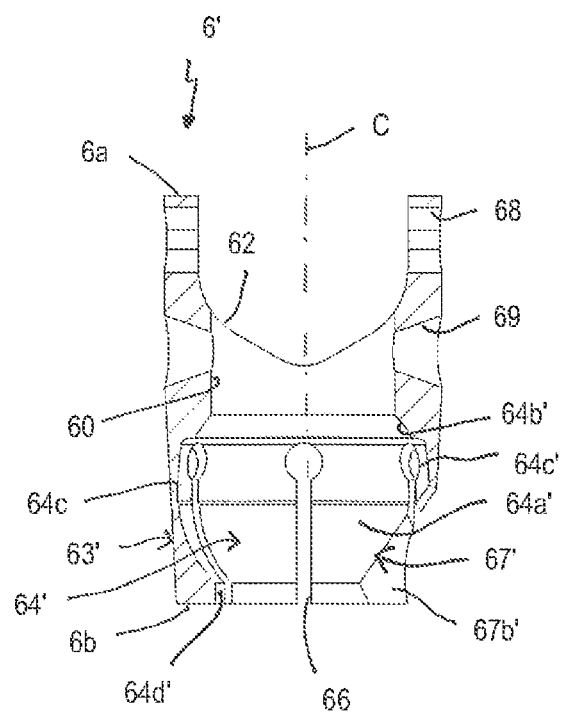
FIG. 23 shows a cross-sectional view of the pressure member of FIGS. 20 to 22, the cross-section taken along line G-G in FIG. 22.

Referring now in greater detail to FIGS. 20 to 23, the pressure member 6' of the second embodiment differs from the pressure member 6 of the first embodiment in the design of the lower portion that facilitates the enlarged pivot angle. The pressure member 6' lacks the inclined edge of the opening of the head receiving recess 64. Instead, the head receiving recess 64' extends with the lower spherical section 64a', the upper spherical section 64b', and the intermediate widening section 64c', around the central longitudinal axis C except in a cut-out portion with an edge 67'. The edge 67' of the cut-out portion has a shape such that, as shown in FIGS. 14 and 15, the shank 2 with its neck 21 can extend therein and is simultaneously prevented from rotation around the central longitudinal axis C. The cut-out portion extends to a height from the bottom end 6b, such that the cut-out portion 56' of the receiving part 5' and the cut-out portion of the pressure member 6' are aligned when the pressure member is mounted to the receiving part 5'. An outer portion 67b' of the edge 67' may be beveled.

Moreover, the head receiving recess 64' may have, adjacent to the bottom end 6b, a substantially cylindrical section 64d' which limits the second maximum pivot angle in a direction opposite to the cut-out to substantially 0° or exactly 0°. The cylindrical section 64d' may be coaxial with the central longitudinal axis C and has a size such that it substantially matches the radius of the neck portion 21. Thereby, the neck portion 21 of the shank 2 abuts against not only an edge of the pressure member but a two-dimensional abutment instead.

Referring to FIGS. 14 and 15 in greater detail, when the bone anchoring element 1 and the pressure member 6' are mounted to the receiving part, the bone anchoring element can be pivoted to one side in a direction of the cut-out to a first maximum pivot angle, and can be pivoted in the opposite direction to a second maximum pivot angle which may be substantially 0° or exactly 0°, depending on the exact geometry. It shall be understood that the cut-outs can also be provided at other positions, so that the bone anchoring element can assume an angle with respect to the transverse axis T which is different from 90°. Also, several cut-outs for providing several first maximum pivot angles may be provided.

Figure 24:
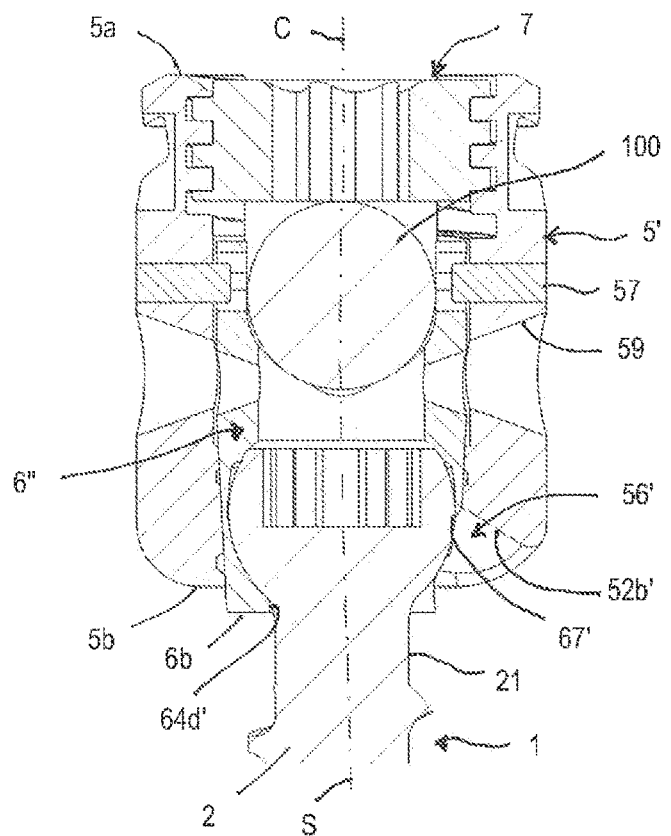
FIG. 24 shows a cross-sectional view of a modified second embodiment of the polyaxial bone anchoring device, with a bone anchoring element of the polyaxial bone anchoring device assuming a second maximum pivot angle, the cross-section taken in a plane including a longitudinal axis of a receiving part of the polyaxial bone anchoring device and extending through centers of legs of the receiving part.
Figure 25:
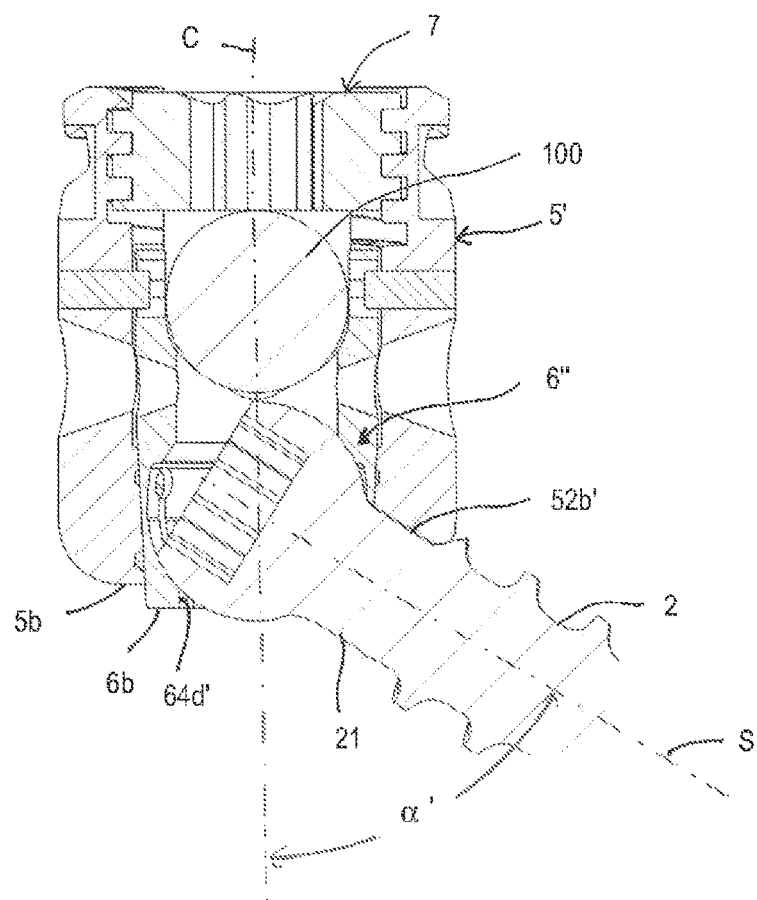
FIG. 25 shows a cross-sectional view of the polyaxial bone anchoring device of FIG. 24, with the bone anchoring element assuming a first maximum pivot angle.

Referring to FIGS. 24 and 25, a modified second embodiment will be described. The modified second embodiment differs from the second embodiment only in that the pressure member 6" is shaped and mounted such that the bottom end 6b of the pressure member 6" is configured to project out of the bottom end 5b of the receiving part 5'. As in the second embodiment, the cylindrical section 64d' of the head receiving recess 64' forms an abutment for the shank 2, more particularly for the neck portion 21 of the shank 2 when the bone anchoring element is pivoted to the second maximum angle opposite to the first maximum angle, which may be a zero position as shown in FIG. 24.

When the bone anchoring element 1 is pivoted so that the shank 2 extends into the cut-out 56 ' and abuts against the edge portion 52b' of the cut-out 56' of the receiving part 5', the pivot angle may be slightly increased compared to the second embodiment.

It shall be noted that the pressure member 6" may be different from the pressure member 6' in that its lower portion is longer to project out of the bottom end 5b. Alternatively, the pressure member 6" may be identical to the pressure member 6' of the second embodiment, but may be insertable more deeply into the receiving part, so that the bottom end 6b can project or project farther out of the lower opening 52 of the receiving part 5'. Therefore, with the same pressure member, slightly different first maximum pivot angles can be achieved.

Further modifications of the above described embodiment are also conceivable. In particular, features of one embodiment can be combined with the features of other embodiments. Such modifications and variations are intended to be included within the scope of the present invention.

The inclined surface at the lower portion of the receiving part may be oriented at various other angles relative to the rod axis.

The second maximum pivot angle in the opposite direction may be greater than about 10°, as long as it is smaller than the first maximum pivot angle.

While the bone anchoring device is shown as a top-loading bone anchoring device in which the bone anchoring element is inserted from the top end into the receiving part, a bottom-loading bone anchoring device may also be conceivable, where the pressure member can be preassembled with the receiving part and the bone anchoring element can be inserted from the bottom end of the receiving part. The receiving part can also have many different shapes. Instead of two elongate recesses and/or two tool engagement recesses, only one of each may be sufficient, or they can be omitted altogether.

While the head is shown to have an overall spherical segment-shape, the head and the pressure member may also be designed so as to allow pivoting only in one or more single planes. In another embodiment, the pressure member may lack the rod receiving recess, and may, for example, be rotatable within the receiving part. Alternatively, the pressure member may have a channel for the rod that is deeper than the rod diameter, in which case the locking member may be a two-part device that includes an outer screw for locking the head and an inner screw for locking the rod independently.

While the embodiments are shown with a rod for connecting several receiving parts, the coupling device may also be a bone plate. In such a case, the receiving part and the pressure member may not include rod receiving recesses, and the passage may be a hole in the bone plate which receives the pressure member.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A coupling device for use with a bone anchoring element comprising a head and a shank for anchoring in bone, the coupling device comprising:
a receiving part connectable to the head of the bone anchoring element, the receiving part having a first end, a second end, and a longitudinal axis extending between respective centers of the first and second ends, and defining a coaxial passage extending from the first end towards the second end;
a pressure member comprising a non-expandable first portion and a radially expandable second portion that forms a seat for the head, the second portion defining an opening and at least one slot extending axially from the opening that forms at least one flexible wall portion, wherein the first and second portions are restricted from separating from one another while the pressure member is free of forces from outside the pressure member acting thereon, and wherein the pressure member is movable in the passage to a position where the receiving part acts on the second portion to exert pressure on and lock the head when the head is held in the seat;
wherein when the pressure member is in the receiving part, a maximum height of the entire pressure member measured in a direction of the longitudinal axis is shorter than a height of the receiving part measured in the direction of the longitudinal axis, the seat is configured to be arranged asymmetrically relative to the longitudinal axis of the receiving part while a central axis of the first portion of the pressure member is substantially coaxial with the longitudinal axis, such that the seat facilitates pivoting of a connected bone anchoring element in at least a first direction at a first maximum angle relative to the longitudinal axis and a second direction opposite the first direction at a second maximum angle relative to the longitudinal axis that is smaller than the first maximum angle, with a portion of the opening located in the first direction being positioned closer axially to a closed end of the slot than to a portion of the opening located in the second direction.

2. The coupling device of claim 1, wherein a wall thickness of the second portion of the pressure member is greater in the second direction than in the first direction.

3. The coupling device of claim 1, wherein the second maximum angle is substantially 0° relative to the longitudinal axis.

4. The coupling device of claim 1, wherein the opening of the pressure member has a non-circular profile.

5. The coupling device of claim 4, wherein the opening is substantially elliptical.

6. The coupling device of claim 1, wherein the opening of the pressure member has a cut-out in the first direction to permit the bone anchoring element to pivot to the first maximum angle in the first direction.

7. The coupling device of claim 1, wherein the second portion of the pressure member comprises a surface in the second direction that extends vertically to facilitate increased contact with the shank.

8. The coupling device of claim 1, wherein the pressure member is configured to extend out of the second end of the receiving part.

9. The coupling device of claim 1, wherein the receiving part defines an opening at or near the second end of the receiving part that is arranged asymmetrically relative to the longitudinal axis of the receiving part.

10. The coupling device of claim 1, wherein the first and second portions of the pressure member are monolithically formed with one another.

11. A bone anchoring device comprising:
a bone anchoring element comprising a head and a shank for anchoring in bone; and
a coupling device for use with the bone anchoring element, the coupling device comprising:
a receiving part connectable to the head, the receiving part having a first end, a second end, and a longitudinal axis extending between the first and second ends, and defining a coaxial passage extending from the first end towards the second end;
a pressure member comprising a non-expandable first portion and a radially expandable second portion that forms a seat for the head, the second portion defining an opening and at least one slot extending axially from the opening that forms at least one flexible wall portion, wherein the first and second portions are restricted from separating from one another while the pressure member is free of forces from outside the pressure member acting thereon, and wherein the pressure member is movable in the passage to a first position where the receiving part acts on the second portion to exert pressure on and lock the head when the head is held in the seat;
wherein when the pressure member is in the receiving part with a central axis of the first portion of the pressure member extending substantially coaxially with the longitudinal axis and when the head is held in the seat, the bone anchoring element is pivotable in at least a first direction at a first maximum angle relative to the longitudinal axis and a second direction opposite the first direction at a second maximum angle relative to the longitudinal axis that is smaller than the first maximum angle, with a portion of the opening located in the first direction being positioned closer axially to a closed end of the slot than to a portion of the opening located in the second direction,
wherein when the pressure member is at the first position and the bone anchoring element is pivoted in the first direction at the first maximum angle, the bone anchoring element directly contacts the receiving part, and wherein when the pressure member is at the first position and the bone anchoring element is pivoted in the second direction at the second maximum angle, the pressure member prevents the bone anchoring element from directly contacting the receiving part.

12. The bone anchoring device of claim 11, wherein the pressure member forms an abutment that limits the pivoting of the bone anchoring element in the second direction.

13. The bone anchoring device of claim 12, wherein when the head is in the seat and the bone anchoring element is pivoted in the second direction, a neck of the bone anchoring element located between the head and the shank is configured to abut against the abutment.

14. The bone anchoring device of claim 13, wherein the abutment extends vertically to facilitate increased contact with the neck of the bone anchoring element.

15. The bone anchoring device of claim 12, wherein the opening is sized for inserting the head into the seat, and wherein an edge of the opening comprises the abutment.

16. The bone anchoring device of claim 12, wherein a wall thickness of the second portion of the pressure member is greater in the second direction corresponding to the abutment than in the first direction.

17. The bone anchoring device of claim 11, wherein the second maximum angle is substantially 0° relative to the longitudinal axis.

18. The bone anchoring device of claim 11, wherein the second portion of the pressure member is configured to extend over at least part of a region of the head that defines a greatest width of the head.

19. The bone anchoring device of claim 11, wherein the seat is configured to clamp the head by friction prior to final locking of the head relative to the receiving part.

20. The bone anchoring device of claim 11, wherein the receiving part forms an abutment that limits the pivoting of the bone anchoring element in the first direction.

21. The bone anchoring device of claim 11, wherein the receiving part and/or the pressure member facilitate pivoting of the bone anchoring element to a plurality of different maximum angles relative to the longitudinal axis in directions other than the first and second directions.

22. The bone anchoring device of claim 11, wherein the receiving part and/or the pressure member limit pivoting of the bone anchoring element to the second maximum angle in substantially every direction other than the first direction relative to the longitudinal axis.

23. The bone anchoring device of claim 11, wherein when the head is held in the seat, the portion of the opening located in the first direction extends above and exposes at least part of a region of the head that defines a greatest width of the head measured in a direction perpendicular to the central axis of the pressure member.

24. A method for implanting a bone anchoring device into bone, the bone anchoring device comprising a bone anchoring element comprising a head and a shank for anchoring in bone and a coupling device comprising a receiving part, the receiving part having a first end, a second end, and a longitudinal axis extending between respective centers of the first and second ends, and defining a coaxial passage extending from the first end towards the second end, a pressure member comprising a non-expandable first portion and a radially expandable second portion that forms a seat for the head, the second portion defining an opening and at least one slot extending axially from the opening that forms at least one flexible wall portion, wherein the first and second portions are restricted from separating from one another while the pressure member is free of forces from outside the pressure member acting thereon, and wherein when the pressure member is in the receiving part, the seat is configured to be arranged asymmetrically relative to the longitudinal axis of the receiving part while a central axis of the first portion of the pressure member is substantially coaxial with the longitudinal axis, and a locking element, the method comprising:

anchoring the shank of the bone anchoring element to bone;

adjusting an angular position of the receiving part relative to the shank when the pressure member is in the receiving part and the head is held in the seat, wherein the seat facilitates pivoting of the receiving part relative to the bone anchoring element in at least a first direction at a first maximum angle relative to the longitudinal axis and a second direction opposite the first direction at a second maximum angle relative to the longitudinal axis that is smaller than the first maximum angle, with a portion of the opening located in the first direction being positioned closer axially to a closed end of the slot than to a portion of the opening located in the second direction;

advancing the locking element in the passage to move the pressure member in the passage to a position where the receiving part acts on the second portion to exert pressure on and lock the head relative to the receiving part.

25. The method of claim 24, wherein the receiving part defines a transverse recess for receiving a rod, and wherein the first portion of the pressure member is configured to extend into the recess to contact the rod.

\* \* \* \* \*